(12) United States Patent
Stephens et al.

(10) Patent No.: US 10,172,640 B2
(45) Date of Patent: Jan. 8, 2019

(54) DEVICE FOR LIFTING ABDOMINAL WALL DURING MEDICAL PROCEDURE

(71) Applicant: Life Care Medical Devices, Ltd., Falmer, Brighton (GB)

(72) Inventors: Robin Stephens, Burgess Hill (GB); Richard J. Prati, New Smyrna Beach, FL (US)

(73) Assignee: Life Care Medical Devices, Ltd., Falmer, Brighton (GB)

( * ) Notice: Subject to any disclaimer, the term of this patent is extended or adjusted under 35 U.S.C. 154(b) by 0 days.

(21) Appl. No.: 14/689,195

(22) Filed: Apr. 17, 2015

(65) Prior Publication Data

US 2016/0302826 A1    Oct. 20, 2016

(51) Int. Cl.
| | |
|---|---|
| *A61B 17/34* | (2006.01) |
| *A61B 17/02* | (2006.01) |
| *A61M 13/00* | (2006.01) |
| *A61B 17/30* | (2006.01) |

(52) U.S. Cl.
CPC ...... *A61B 17/3423* (2013.01); *A61B 17/0218* (2013.01); *A61B 17/0281* (2013.01); *A61B 2017/308* (2013.01); *A61B 2017/3429* (2013.01); *A61B 2217/005* (2013.01); *A61M 13/003* (2013.01)

(58) Field of Classification Search
CPC ............ A61B 17/3423; A61B 17/0218; A61B 17/3421; A61B 17/0293; A61B 2017/0225; A61B 1/32; A61B 17/02; A61B 17/3439

USPC .................................................. 600/201–209
See application file for complete search history.

(56) References Cited

U.S. PATENT DOCUMENTS

| | | | | |
|---|---|---|---|---|
| 4,633,865 | A | * | 1/1987 | Hengstberger ......... A61B 90/40 600/114 |
| 4,635,618 | A | | 1/1987 | Munz |
| 5,480,410 | A | | 1/1996 | Cuschieri et al. |
| 5,735,791 | A | * | 4/1998 | Alexander, Jr. ......... A61B 17/02 600/207 |
| 5,853,395 | A | * | 12/1998 | Crook ................ A61B 17/3423 600/208 |

(Continued)

FOREIGN PATENT DOCUMENTS

WO     WO 2015172888 A2 *  11/2015 ............. A61B 90/40

*Primary Examiner* — Eduardo C Robert
*Assistant Examiner* — Michelle C Eckman
(74) *Attorney, Agent, or Firm* — Womble Bond Dickinson (US) LLP (57) ABSTRACT

A device for producing a pneumoperitoneum in a medical procedure includes a main body having a ring portion defining a main opening, and a domed portion extending from the ring portion to an apex. The ring portion is adapted to form a positive seal with the skin of the patient upon application of a suction force within the main body abutting the patient. The device includes a suction port extending from the domed portion of the main body and is configured to facilitate application of the suction within the main body. The access port is operably engaged with the domed portion of the main body proximate to the apex and is adapted to receive a surgical instrument therethrough. A pair of opposed grips operably engaged with the domed portion of the main body is adapted to facilitate one-handed application and removal of the main body with respect to the patient.

12 Claims, 6 Drawing Sheets

(56) References Cited

U.S. PATENT DOCUMENTS

| | | | |
|---|---|---|---|
| 5,893,368 A * | 4/1999 | Sugerman | A61H 9/005 128/898 |
| 5,957,931 A * | 9/1999 | Dimitriu | A61B 17/442 604/74 |
| 6,033,426 A * | 3/2000 | Kaji | A61B 17/3423 600/207 |
| 6,042,539 A * | 3/2000 | Harper | A61B 17/0281 600/201 |
| 6,485,467 B1 | 11/2002 | Crook et al. | |
| 7,297,141 B2 * | 11/2007 | Kathrani | A61B 17/3421 604/500 |
| 7,585,281 B2 | 9/2009 | Nezhat et al. | |
| D609,340 S * | 2/2010 | Eder | D24/133 |
| 2004/0030333 A1 * | 2/2004 | Goble | A61B 17/3423 606/41 |
| 2004/0049127 A1 * | 3/2004 | Nezhat | A61B 17/3403 600/564 |
| 2006/0149135 A1 | 7/2006 | Paz | |
| 2007/0270745 A1 * | 11/2007 | Nezhat | A61B 5/6834 604/115 |
| 2008/0058603 A1 * | 3/2008 | Edelstein | A61B 17/3403 600/201 |
| 2008/0058851 A1 * | 3/2008 | Edelstein | A61B 17/3403 606/185 |
| 2008/0262527 A1 * | 10/2008 | Eder | A61B 17/3403 606/185 |
| 2009/0082634 A1 * | 3/2009 | Kathrani | A61B 17/0218 600/207 |
| 2009/0093682 A1 * | 4/2009 | Izzo | A61B 17/3462 600/201 |
| 2009/0093683 A1 * | 4/2009 | Richard | A61B 17/3417 600/204 |
| 2009/0270789 A1 | 10/2009 | Maxymiv et al. | |
| 2010/0210915 A1 * | 8/2010 | Caldwell | A61B 17/0281 600/210 |
| 2010/0274091 A1 * | 10/2010 | Rothstein | A61B 17/3423 600/201 |
| 2011/0230724 A1 * | 9/2011 | Richard | A61B 17/3462 600/208 |
| 2012/0123202 A1 * | 5/2012 | Albrecht | A61B 17/3417 600/104 |
| 2013/0030253 A1 * | 1/2013 | Titus | A61B 17/0281 600/207 |
| 2013/0190572 A1 * | 7/2013 | Lee | A61B 17/0218 600/204 |
| 2013/0190573 A1 * | 7/2013 | Smith | A61B 17/0218 600/207 |
| 2013/0197315 A1 * | 8/2013 | Foley | A61B 17/0281 600/205 |
| 2014/0005474 A1 * | 1/2014 | Farin | A61B 1/00154 600/104 |
| 2014/0046123 A1 * | 2/2014 | Connors | A61F 2/0027 600/31 |
| 2014/0343360 A1 * | 11/2014 | Shohat | A61B 17/3403 600/114 |
| 2015/0133738 A1 * | 5/2015 | Foley | A61B 17/0281 600/204 |
| 2015/0216519 A1 * | 8/2015 | Tang | A61B 17/3423 600/204 |
| 2016/0008081 A1 * | 1/2016 | Forsell | A61B 17/3423 600/204 |

* cited by examiner

DEVICE FOR LIFTING ABDOMINAL WALL DURING MEDICAL PROCEDURE

BACKGROUND

Field of the Disclosure

The present disclosure relates to a device for producing a pneumoperitoneum by elevating skin, subcutaneous tissue and/or muscle of a patient from the underlying organ and/or an anatomical features cavity to facilitate safe entry of a surgical instrument into the cavity during a medical procedure.

Description of Related Art

Some conventional medical procedures require a direct incision of the abdominal wall for insertion of a surgical instrument, such as a trocar, into the patient's body cavity. The incision must be sufficiently large enough to provide for the insertion of the particular surgical instrument utilized by the surgeon, as well as to provide for a viewing space for a medical procedure through insertion of a laparoscope, which may be connected to a video camera with an arrangement to project a magnified view of the operative field onto a monitor for facilitating the performance of a complex medical procedure. A patient's body cavity may be insufflated with an inert gas, such as carbon dioxide ($CO_2$), to elevate an abdominal wall from underlying vital organs within the cavity so as to create a working space for the medical procedure within the patient's body cavity. $CO_2$ is used as it is common to the human body, can be absorbed by tissue, and is a waste product of respiration. In addition, $CO_2$ is not readily combusted by flame which is an advantage as medical procedures and/or surgeries are known to use electrosurgical devices. The presence of gas within the patient's body cavity is known as pneumoperitoneum.

However, the challenge of the conventional approach for accessing a patients' body cavity for a medical procedure lies in the lifting of the abdominal wall wherein, conventionally, devices such as retractors are used to lift the abdominal wall of the patient's body cavity to enable incision or perforation of the patient's abdominal wall by way of trocars. The use of retractors or lifting rods delivers a lifting force for elevation or separation of the skin, subcutaneous tissue and muscle of a patient from the underlying organs or anatomical features cavity to facilitate safe entry of a medical device into the cavity for a medical procedure.

In general, a typical device for elevation of skin, subcutaneous tissue and muscle of a patient from the underlying organs, such as a retractor, tends to be bulky and/or requires a complex installation procedure. Additionally, the lifting force produced by such a bulky device increases the risk of vascular injury as well as incision-related complications, such as a dehiscence and/or a hernia, because of a large incision.

Additional disadvantages of the conventional approach in accessing the abdominal wall of the patient's body cavity include, for example, the creation of the pneumoperitoneum which requires special pumps, pressure gauges, needles, and the possibility of the insufflation gas seeping into the blood stream. In addition, the insufflation gas may periodically seep out of the abdominal cavity which may cause the abdominal wall to fall, thereby interrupting the surgical procedure.

Aspects of the present disclosure utilize negative pressure to raise the abdominal wall above the vital organs to facilitate safe entry of a surgical instrument into the cavity, which may reduce the risk of some complications associated with 'blind entry' and reduce the size of the myofascial defect in the abdominal wall. The methodology of the present disclosure for elevating skin, subcutaneous tissue and muscle of a patient from the underlying organs, which utilizes negative pressure, allows for an insufflation gas (e.g., $CO_2$) to be introduced upon sufficient negative pressurization to maintain the insufflations level of the abdominal cavity such that a surgical instrument may be safely introduced to the patient's target intraventional area for the medical procedure. Thus, aspects of the present disclosure include a variety of advantages over the prior art.

The subject matter claimed herein is not limited to aspects that solve any disadvantages or that operate only in environments such as those described above. Rather, this background is only provided to illustrate one exemplary technological area where some aspects described herein can be utilized.

BRIEF SUMMARY OF THE DISCLOSURE

The above and other needs are met by aspects of the present disclosure which, in one aspect, provides a device for producing a pneumoperitoneum during a medical procedure. The device may include a main body that has a ring portion defining a main opening and a domed portion that extends from the ring portion to an apex. The ring portion may be adapted to form a positive seal with the skin of the patient upon application of a suction force within the main body abutting the patient.

According to some aspects, the device may further include a suction port that extends from the domed portion of the main body and is configured to facilitate application of the suction within the main body. Additionally, the device may include an access port that is operably engaged with the domed portion of the main body proximate to the apex. The access port may be adapted to receive a surgical instrument therethrough. Further, the device may include a pair of opposing grips that are operably engaged with the domed portion of the main body. The opposed grips may be adapted to facilitate one-handed application and removal of the main body of the device with respect to the patient. One of more features of the device may taper or converge away from the ring portion toward the apex so as to, for example, facilitate release of the device from a mold.

These and other features, aspects, and advantages of the disclosure will be apparent from a reading of the following detailed description together with the accompanying drawings, which are briefly described below.

BRIEF DESCRIPTION OF THE DRAWINGS

Having thus described the disclosure in the foregoing general terms, reference will now be made to the accompanying drawings, which are not necessarily drawn to scale, and wherein:

DETAILED DESCRIPTION OF THE DISCLOSURE

The present disclosure will now be described more fully hereinafter with reference to exemplary aspects thereof. These exemplary aspects are described so that this disclosure will be thorough and complete, and will fully convey the scope of the disclosure to those skilled in the art. Indeed, the disclosure may be embodied in many different forms and should not be construed as limited to the aspects set forth herein; rather, these aspects are provided so that this disclosure will satisfy applicable legal requirements. As used in the specification, and in the appended claims, the singular forms "a", "an", "the", include plural referents unless the context clearly dictates otherwise.

The present disclosure is directed to a device, and a method for producing such a device, that creates a pneumoperitoneum for facilitating a medical procedure. More particularly, aspects of the present disclosure relate to a device that provides for elevating skin, subcutaneous tissue, muscle and/or the like of a patient to facilitate safe entry of a surgical instrument into a cavity produced thereby for conducting a medical procedure. Elevation of the skin, subcutaneous tissue, muscle and/or the like is accomplished, in part, by raising the abdominal wall above the underlying organs or anatomical features cavity through a pneumatic arrangement.

Figure 1:
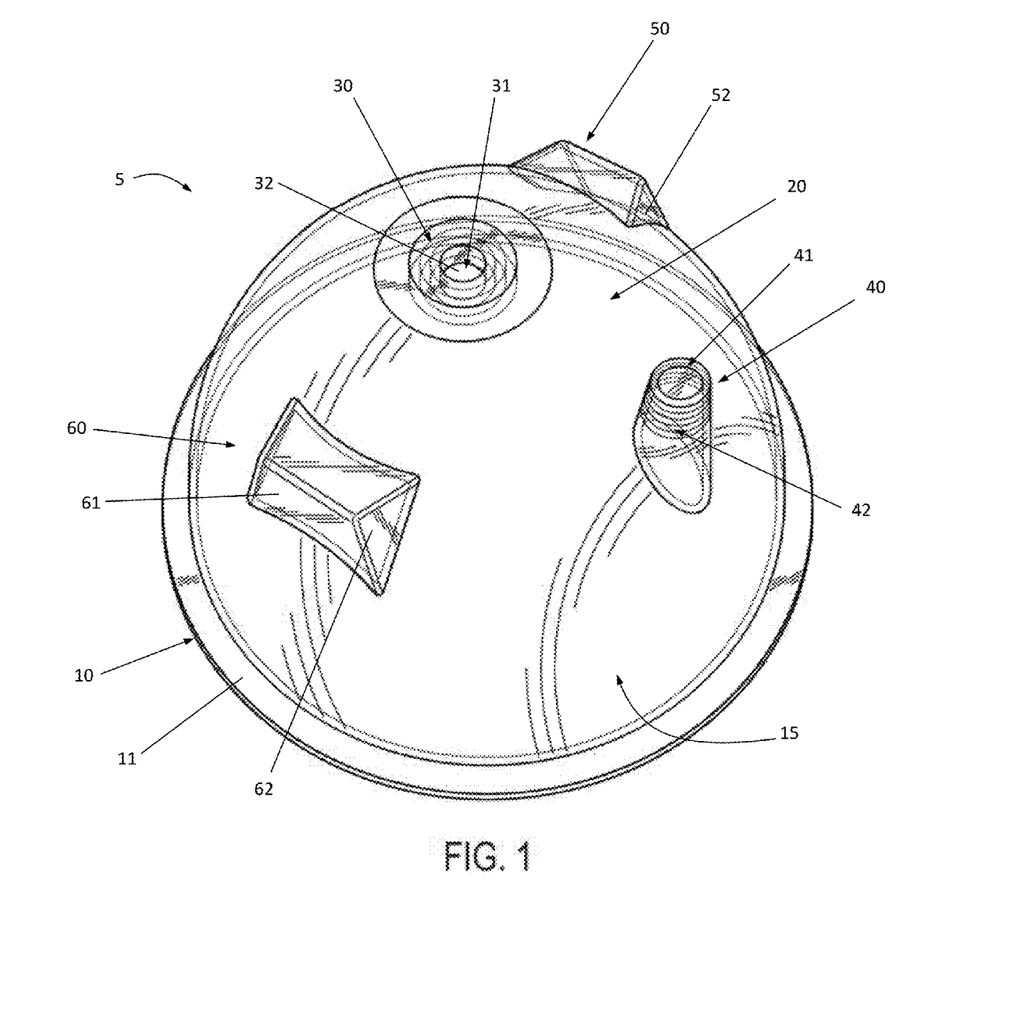
FIG. 1 illustrates a perspective view of a device for performing a medical procedure by producing a pneumoperitoneum according to an example aspect of the present disclosure.

FIG. 1 illustrates a representative medical device for producing a pneumoperitoneum for conducting a medical procedure. According to aspects of the present disclosure, the device may include a main body 5 that includes a ring portion 10 and a domed portion 20. The domed portion 20 extends upwards from the ring portion 10 toward an apex, while the ring portion extends circumferentially about the main body 5. Further, the ring portion 10 may define a main opening 15, which may provide access to the interior volume defined by the domed portion 20.

The ring portion 10 of the main body 5 may include a flange 11 that extends radially outward from the domed portion 20. According to some aspects, the flange 11 may further define a bottom surface that defines a plane. The bottom surface of the flange 11 may be substantially planar and/or flat. However, one skilled in the art will appreciate that the bottom surface of the flange 11 may otherwise be regularly or irregularly configured, as necessary or desired, in order to accomplish the functions and purposes disclosed herein. In one instance, the device may be configured such that, when the ring portion 10/flange 11 of the device is placed on a patient's skin and a suction force is imparted within the domed portion of the main body, the ring portion interacts with the skin of the patient to provide a positive seal, facilitated by a vacuum or suction, between the device and the skin of the patient. Accordingly, the device may be placed onto a patient's target medical intraventional area and secured to the patient, without using fasteners or extraneous mechanical fastening arrangements. According to some aspects of the present disclosure, a substantially planar and/or flat bottom surface of the flange 11 may advantageously provide for an improved interaction between the ring portion of the device and the skin of the patient as the substantially planar and/or flat bottom surface of the flange provides for increased surface contact between the device and the patient's skin. As such, some aspects provide for an improved suction and/or vacuum connection between the device and the skin of the patient for securing the device to the patient without using additional and/or extraneous mechanical fastening arrangements.

Figure 3:
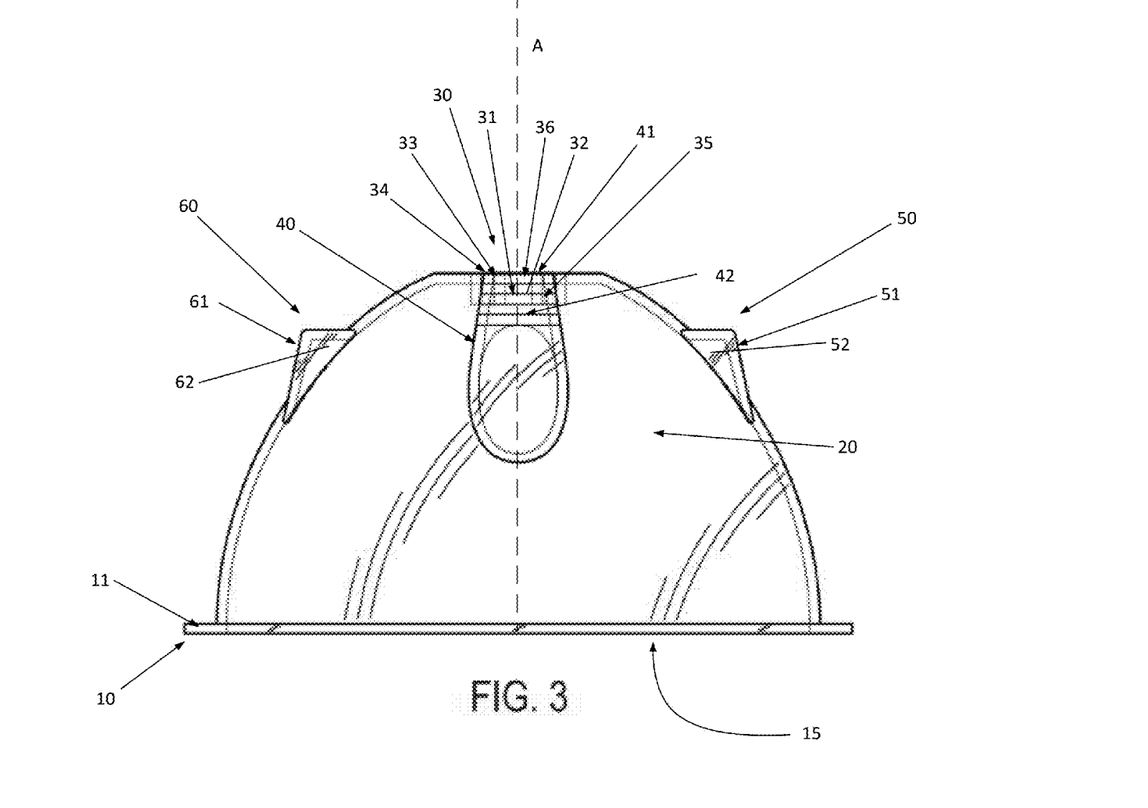
FIG. 3 illustrates a side view of a device for performing a medical procedure by producing a pneumoperitoneum according to an example aspect of the present disclosure.

In some aspects, the main body 5 may further define an axis A that extends perpendicularly to the plane defined by the bottom surface of the flange 11 of the ring portion 10, as shown in FIG. 3. In addition, the axis A may extend perpendicularly to the plane and through the apex, wherein the apex also defines a maxima of the domed portion 20. In some aspects, the ring portion 10 of the main body is substantially circular in shape and defines a center that coincides with the intersection of the axis A and the plane defined by the ring portion. Although aspects herein illustrate the ring portion being substantially circular in shape, other shapes (e.g., square, rectangular, triangular, etc.) also are encompassed within the present disclosure.

The device may further include an access port 30 that is disposed proximate the apex of the domed portion 20. According to one aspect, the access port 30 may coincide with the apex of domed portion of the main body. Accordingly, the axis A may extend longitudinally through the access port 30. The access port 30 may be further configured to receive a surgical instrument therethrough. Specifically, the access port 30 may include an annular seat 35 defining an opening 31 and include a septum 32 that engages the annular seat and extends across the opening 31. According to some aspects, the septum 32 may be configured to form a seal about a surgical instrument such as, for example, a veress needle, after the surgical instrument penetrates through the septum of the access port 30 into the main body. As such, the septum 32 allows for the surgical instrument to be inserted within the domed portion 20 of the main body 5 while maintaining a positive seal about the surgical instrument, such that pressure or suction can be maintained by the domed portion of the main body. Additionally or alternatively, the seal formed by the septum 32 about a surgical instrument, after the surgical instrument has penetrated through the septum, may prevent insufflation gas from escaping from the interior volume defined by the domed portion 20.

Figure 6:
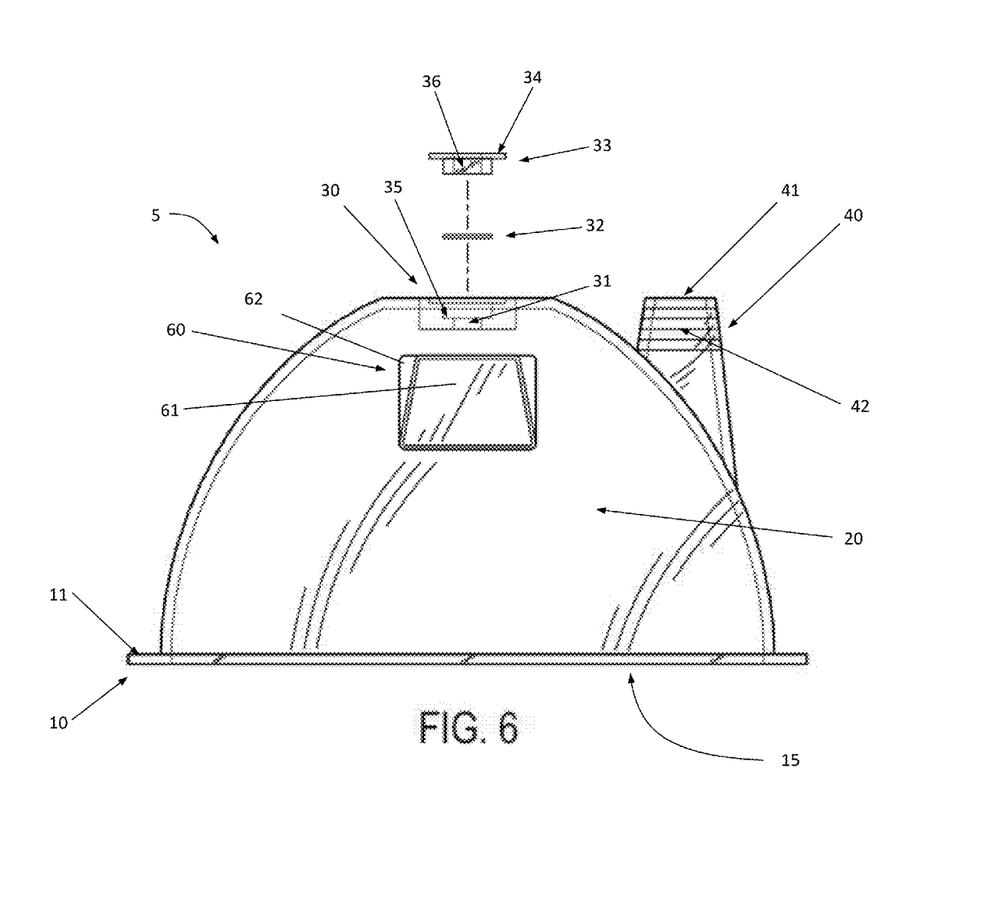
FIG. 6 illustrates an exploded side view of a device for performing a medical procedure by producing a pneumoperitoneum according to an example aspect of the present disclosure.

In some aspects, the septum 32 may comprise a silicone material, polysiloxane, and/or any other suitable polymeric or other material configured to form a seal about a surgical instrument after the surgical instrument penetrates through the septum. According to one aspect, the septum 32 may be securely attached to the domed portion 20 of the main body, proximate the opening 31, with a clamping ring 33 configured to engage the annular seat and secure the septum 32 therebetween. In some aspects, the clamping ring 33 may comprise a poly-carbonate material configured to operably engage the annular seat and to thereby securely attach the septum 32 within the access port. As shown in FIG. 6, for example, the access port 30 may include an annular seat 35 that defines the opening 31. The annular seat 35 may be configured to receive the septum 32 such that the septum extends across the entire opening 31. In addition, the clamping ring 33 may further define an opening 36 that coincides with the opening 31 defined by the annular seat. Thereafter, the clamping ring 33 may be securely attached to the annular seat, for example, in a press-fit engagement. For instance, the clamping ring 33 may be securely attached to the annular seat 35 by inserting the clamping ring within the annular seat and pressing a lip portion 34 of the clamping ring into a friction or snap-fit with the annular seat. In some aspects, the lip portion 34 of the clamping ring 33 may be securely engaged with the annular seat 35 by applying a pressing force toward the annular seat at four discrete points disposed about the lip portion. According to one aspect, the four discrete points may be disposed about the lip portion 34 of the clamping mechanism 33 in equally spaced (i.e., 90 degrees) intervals. Although described as having a snap-fit engagement with the annular seat 35, other types of suitable engagement arrangements (e.g., press-fit, magnetic etc.) for the clamping ring 33 are also encompassed by the present disclosure.

According to another aspect, the device may further include a suction port 40. The suction port 40 may extend from the domed portion 20 of the main body 5 and may be configured to facilitate application of a suction force within the main body. For example, the suction port 40 may define a suction port opening 41 that is in fluid communication with a suction port channel 42, which is in fluid communication with the interior volume defined by the domed portion 20 of the main body. As such, the device may be configured to produce a pneumoperitoneum by raising the abdominal wall above the underlying organs of the patient's body cavity, through connection of the suction port 40 to a vacuum system or other pneumatic (suction) arrangement. In one aspect, an external vacuum system (not shown) may be in fluid communication with the interior volume defined by the domed portion 20, through connective tubing and/or other conduit materials that may be coupled with and in fluid communication with the suction port opening 41 and the suction port channel 42. In some instances, a valve or other arrangement for controlling the application of suction via the suction port 40 may be operably engaged between the suction port 40 and the external vacuum system.

In some instances, negative pressure may be introduced into the suction port 40 of the device and may be modulated through the adjustment of the negative pressure level provided by the external vacuum system. As such, a user may ensure that sufficient negative pressure is present to produce a pneumoperitoneum and/or elevate the skin, subcutaneous tissue, and/or muscle of a patient away from the underlying organs within the patient's body cavity. In any instance, after formation of the pneumoperitoneum, an inert gas, such as $CO_2$, which is common to the human body, may be introduced into the patient's body cavity by inserting an instrument through the septum 32 of the access port 30 and into the cavity. When negative pressure forming the pneumoperitoneum reaches a sufficient level, the inert gas introduced into the cavity may cause, increase, and/or otherwise enhance separation between the skin, subcutaneous tissue, and muscle from the underlying organs within the patient's body cavity over that provided by the negative pressure.

According to one aspect, the suction port 40 may extend from the domed portion of the main body, and away from the ring portion 10. In one aspect, the suction port 40 may extend outwardly from the domed portion along a direction that is parallel with the axis A, as shown in FIG. 3. In some aspects, the suction port 40 may be shaped as a substantially tapered cylinder and/or may be shaped to taper away from the ring portion 10 as the suction port 40 extends from the domed portion of the main body. For example, the external diameter of the suction port channel 42 may decrease in size as the suction port 40 extends from the domed portion 20 of the main body 5. In addition, the internal diameter of the suction port channel 42 may increase in size from the suction port opening 41 to the entrance to the internal volume defined by the domed portion 20 of the main body 5. Although the suction port 40 is shaped substantially as a tapered cylinder, additional aspects of the present disclosure encompass alternative configurations of the suction port. For example, the suction port 40 may be shaped as a tapered cuboid, pyramid, and/or the like. As discussed further herein, the tapered shape of the suction port 40 and other components of the main body 5 may provide particular advantages during use, such as ease of operation, and during manufacturing of the device, such as ease of production (i.e., in a molding process). More particularly, the tapered configurations disclosed herein may facilitate the release of the device from a mold.

Figure 2:
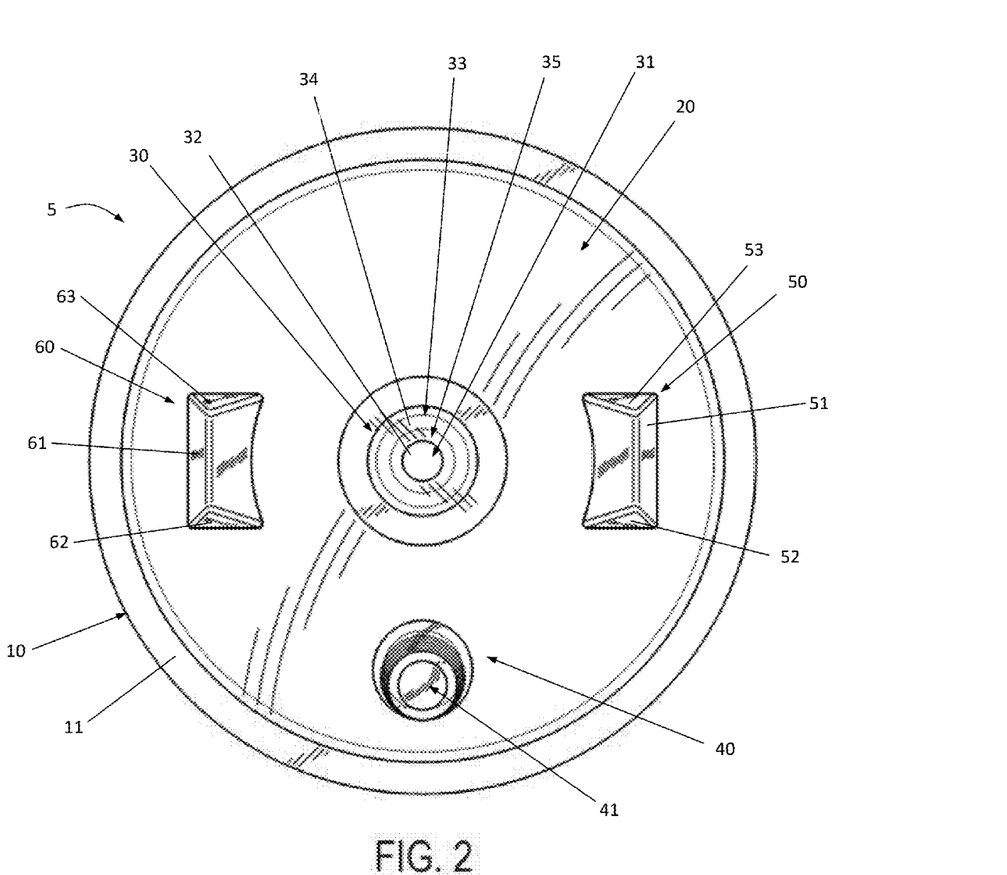
FIG. 2 illustrates a top view of a device for performing a medical procedure by producing a pneumoperitoneum according to an example aspect of the present disclosure.

Referring to FIG. 1, the device may further include a pair of opposing grips 50, 60 that are operably engaged with the domed portion 20 of the main body 5. The opposing grips 50, 60 may be adapted to facilitate one-handed operation, application, and/or removal of the device with respect to the patient. According to one aspect, the opposing grips 50, 60 may be disposed opposite from one another along the domed portion 20 and/or equidistant from the apex and/or access port 30. For example, the grips 50, 60 may be diametrically opposed to one another, and when viewed from above, as in FIG. 2, the access port 30, apex, and/or axis A may bisect the distance between the two opposing grips 50, 60.

According to one aspect, the opposing grips 50, 60 may each define a respective gripping surface 51, 61 that is configured to converge toward the axis A and/or access port 30 of the main body away from the ring portion 10. Additionally and/or alternatively, the opposing grips 50, 60 may also each include respective side surfaces 52, 53, 62, 63 that also taper upwards and away from the ring portion 10 in a similar manner as the gripping surfaces 51, 61. The tapered shape of the respective gripping and side surfaces of the opposing grips may provide for particular advantages, such as ease of operation during use and/or ease of manufacturing during production of such a device (i.e., release of the device from a mold in a molding process). In some aspects, the tapered gripping surfaces 51, 61 may provide for increased control during placement of the device on a patient's skin, during a procedure that produces a pneumoperitoneum, by providing a user with a more ergonomically desired position to grip, engage, hold, and/or position the device, and/or by providing a device that can be implemented with one hand. Additionally or alternatively, the substantially tapered shape of the gripping surfaces and/or the side surfaces may provide for more efficient manufacturing of the device by decreasing the amount of time and effort when removing the device from a mold during a molding process, such as an injection molding process.

Figure 4:
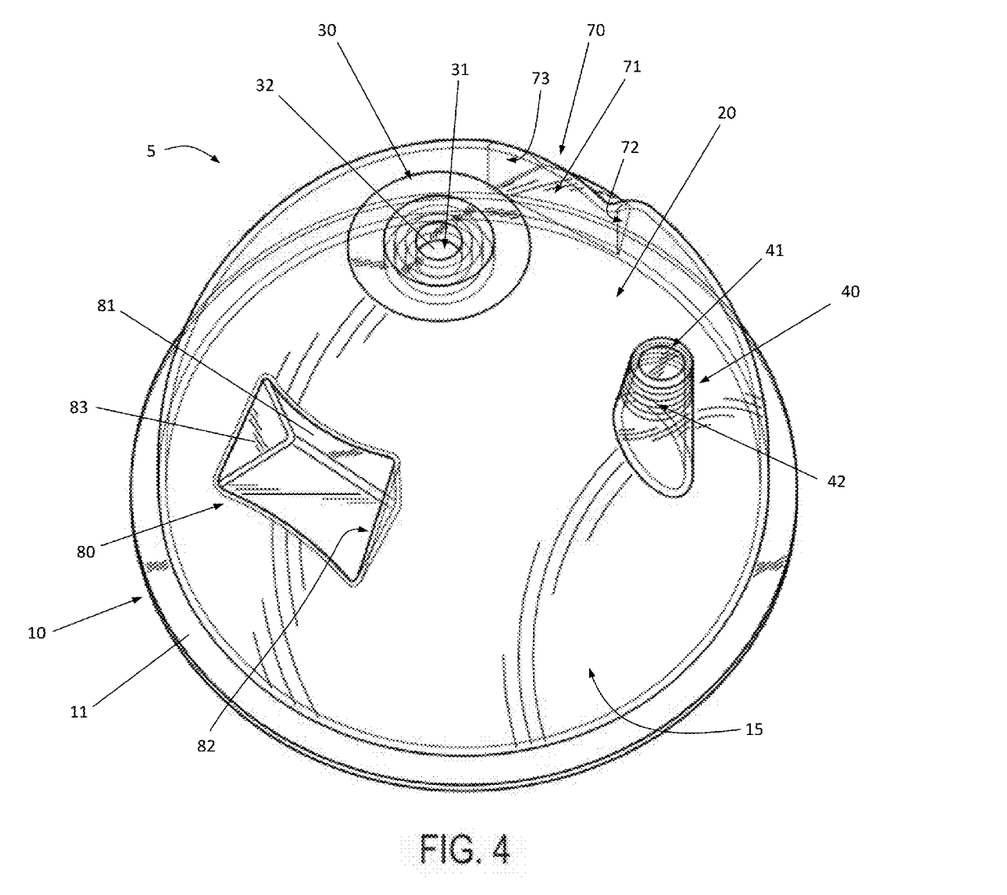
FIG. 4 illustrates a perspective view of a device for performing a medical procedure by producing a pneumoperitoneum according to an example aspect of the present disclosure.
Figure 5:
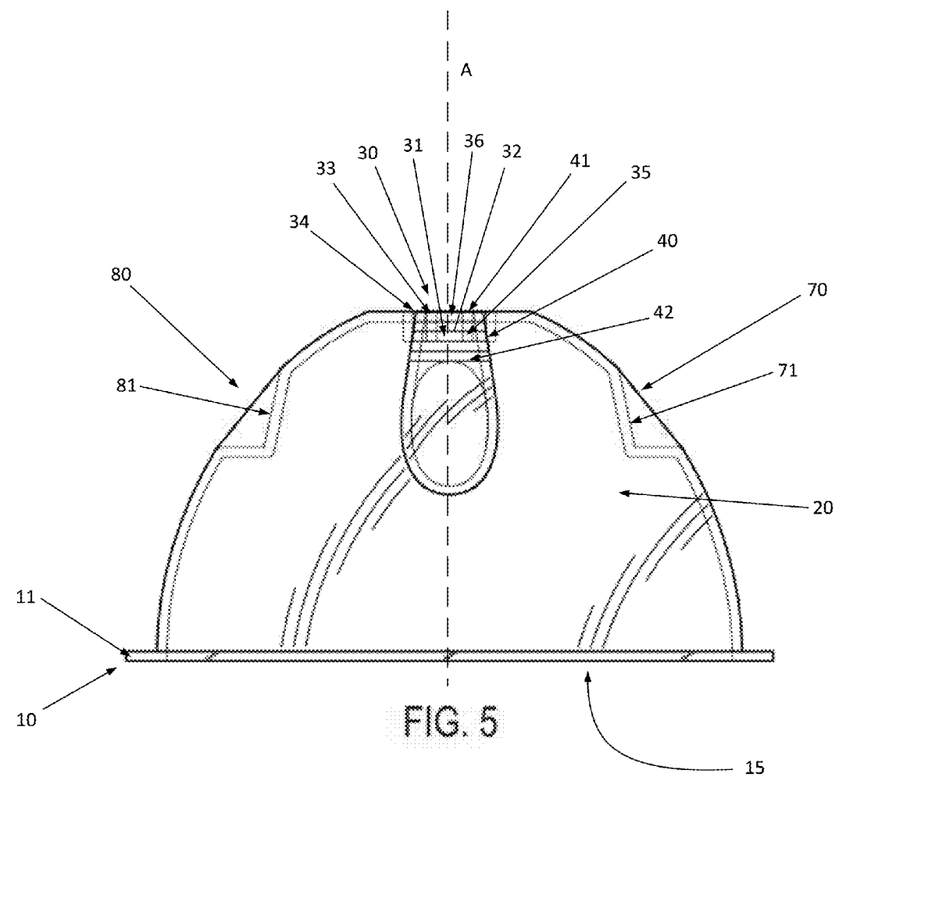
FIG. 5 illustrates a side view of a device for performing a medical procedure by producing a pneumoperitoneum according to an example aspect of the present disclosure.

According to one aspect, the pair of opposing grips 50, 60 may extend outwardly from the domed portion 20 of the main body 5, as shown in FIG. 3. According to another aspect, the pair of opposing grips 70, 80 may extend inwardly into the domed portion 20 of the main body 5, as shown in FIGS. 4 and 5. As illustrated in FIG. 5, the tapered gripping surfaces 71, 81 may also provide for increased control during placement of the device on a patient's skin, during a procedure that produces a pneumoperitoneum, by providing a user with a more ergonomic position to grip, engage, hold, and/or position the device, and/or by providing a device that can be implemented with one hand. In addition, the respective side surfaces 72, 73, 82, 83 may also be substantially tapered, as shown in FIG. 4, so as to provide for more efficient manufacturing of the device by decreasing the amount of time and effort when removing the device from a mold during a molding process, such as an injection molding process.

According to one aspect, a method for performing a pneumoperitoneum procedure may include placing the ring portion 10 of the device on a patient's target medical intraventional area. A vacuum or suction system may be attached to the suction port 40 via a conduit and/or tubing that is in fluid communication between the suction port and the vacuum/suction system. The vacuum/suction provided by the vacuum system may be controlled or otherwise modulated, as necessary or desired. The vacuum system may then provide a suctioning force that produces a negative pressure onto the target body area of the patient, thereby creating a pneumoperitoneum. Subsequently, the user may then insert a surgical instrument through the access port 30 thereby penetrating the septum and allowing the surgical instrument to access to the interior volume defined by the domed portion of the main body. According to one aspect, a surgical instrument may be inserted into the patient's body cavity through the access port 30 located proximate the apex of the domed portion. Additionally or alternatively, a surgical instrument may be inserted directly into the cavity of the patient's abdomen and/or other target intraventional area formed by the pneumoperitoneum, more particularly with the distal end of the surgical instrument projecting into the patient's body cavity upon elevation of the skin, subcutaneous tissue, and/or muscle of the patient from the underlying organs of the patient's body cavity.

The device of the present disclosure and method of use and/or manufacture may thus advantageously prevent collapse of the abdominal wall of the patient's body cavity by introducing sufficient negative pressure external to the cavity and an insufflation inert gas within the cavity, which thus facilitates safe entry of other surgical instruments via the access port 30, as necessary or desired. Safe entry of such further surgical instruments into the patient's body cavity may facilitate less scarring, as well as provide a less traumatic surgical operation. The device of the present disclosure as described herein is intended to provide a simple, yet versatile and convenient device for use in operating theatres so as to assist surgeons in a medical procedure, but is also configured and arranged so as to facilitate (simplify) manufacturing, as well as facilitate implementation in the described surgical procedure using one hand.

The present disclosure may be embodied in other forms without departing from its essential characteristics. The described aspects are to be considered in all respects only as illustrative and not restrictive. The scope of the disclosure is, therefore indicated by the appended claims rather than by the foregoing description. All changes, which come within the meaning and range of equivalency of the claims, are to be embraced within their scope.

Many modifications and other aspects of the disclosure will come to mind to one skilled in the art to which this disclosure pertains having the benefit of the teachings presented in the foregoing descriptions and the associated drawings. Therefore, it is to be understood that the disclosure is not to be limited to the specific aspects disclosed herein and that modifications and other aspects are intended to be included within the scope of the appended claims. Although specific terms are employed herein, they are used in a generic and descriptive sense only and not for purposes of limitation.

That which is claimed:

1. A device for producing a pneumoperitoneum in a medical procedure, the device comprising:
   a main body having a ring portion defining a main opening, and a domed portion extending from the ring portion to an apex, the ring portion being adapted to form a positive seal with the skin of the patient upon application of a suction within the main body abutting the patient, wherein the ring portion of the main body defines a plane, and the main body further defines an axis extending perpendicularly to the plane and through the apex;
   a suction port extending from the domed portion of the main body and configured to facilitate application of the suction within the main body;
   an access port operably engaged with the domed portion of the main body proximate to the apex, the access port being adapted to receive a surgical instrument therethrough; and
   a pair of opposed grips operably engaged with the domed portion of the main body, the opposed grips being adapted to facilitate one-handed application and removal of the main body with respect to the patient, wherein a laterally outermost surface of each grip defines a gripping surface, each laterally outermost surface intersecting and extending directly from the main body, and each laterally outermost surface being configured to converge toward the axis of the main body away from the ring portion, and wherein tapered side surfaces are configured to extend from opposed sides of the laterally outermost surface and intersect with the domed portion.

2. The device according to claim 1, wherein the access port is configured to coincide with the apex of the main body.

3. The device according to claim 1, wherein the suction port extends from the domed portion of the main body, and away from the ring portion, in parallel with the axis.

4. The device according to claim 3, wherein the suction port is configured to taper away from the ring portion.

5. The device according to claim 1, wherein each of the pair of opposed grips extends outwardly of the domed portion of the main body.

6. The device according to claim 5, wherein each gripping surface further defines a gripping arrangement adapted to facilitate increased grip for application and removal of the main body with respect to the patient.

7. The device according to claim 1, wherein each of the pair of opposed grips extends into the domed portion of the main body.

8. The device according to claim 7, wherein each gripping surface further defines a gripping arrangement adapted to facilitate increased grip for application and removal of the main body with respect to the patient.

9. The device according to claim 1, wherein the access port further defines an opening and includes a septum extending across the opening, the septum being configured to form a seal about the surgical instrument following insertion therethrough into the main body.

10. The device according to claim 9, wherein the septum is comprised of a silicone material.

11. The device according to claim 9, wherein the access port further includes an annular seat configured to receive the septum and to form a sealing engagement therewith.

12. The device according to claim 11, wherein the annular seat is further configured to receive a clamping ring configured to operably engage the annular seat so as to secure the septum therebetween.

* * * * *